United States Patent [19]

Nickles

[11] 4,033,335

[45] July 5, 1977

[54] METHOD AND APPARATUS FOR MULTIPLEXING OF PHYSIOLOGICAL SENSOR SIGNALS WITH GAMMA RAY CAMERA DATA SIGNALS

[75] Inventor: Robert J. Nickles, Madison, Wis.

[73] Assignee: Wisconsin Alumni Research Foundation, Madison, Wis.

[22] Filed: June 12, 1975

[21] Appl. No.: 586,200

[52] U.S. Cl. .......................... 128/2.05 R; 128/2 A
[51] Int. Cl.² .......................................... A61B 5/02
[58] Field of Search ............. 128/2 A, 2 R, 2.06 R, 128/2.1 A, 2.1 R, 2.05 R

[56] References Cited

UNITED STATES PATENTS

| | | | |
|---|---|---|---|
| 2,933,081 | 4/1960 | Passannante | 128/2.06 R |
| 3,210,747 | 10/1965 | Clynes | 128/2.1 A |
| 3,220,404 | 11/1965 | Del Lucchese | 128/2.05 R |
| 3,465,103 | 9/1969 | Lynch | 128/2.1 A |
| 3,572,316 | 3/1971 | Vogelman et al. | 128/2.05 R |
| 3,590,811 | 7/1971 | Harris | 128/2.06 R |
| 3,769,966 | 11/1973 | Youdin et al. | 128/2 A |

FOREIGN PATENTS OR APPLICATIONS 965,738   2/1950   France .......................... 128/2.06 R Primary Examiner—William E. Kamm
Attorney, Agent, or Firm—Theodore J. Long; John M. Winter; Harry C. Engstrom

[57] ABSTRACT

A method and device for multiplexing time varying amplitude physiological data signals with the signals provided by the photomultiplier tubes of a gamma ray scintillation camera. The time varying amplitude signals from physiological sensors are converted to a series of uniformly shaped pulses having a pulse frequency which is directly proportional to the amplitude of the physiological signal. The pulses are shaped to correspond to the shape and size of significant pulses provided at the output circuitry of the photomultiplier tubes of the camera. The shaped pulses are combined with the pulses provided by a photomultiplier tube, and are processed by the internal circuitry of the gamma ray camera in the same manner as gamma ray scintillation data. A computer can be utilized to process the data thus provided, and to display the gamma ray scintillation data in time synchrony with the physiological signal source data.

5 Claims, 4 Drawing Figures

METHOD AND APPARATUS FOR MULTIPLEXING OF PHYSIOLOGICAL SENSOR SIGNALS WITH GAMMA RAY CAMERA DATA SIGNALS

BACKGROUND OF THE INVENTION

1. Field of the Invention

This invention pertains generally to the field of physiological data recording and transmission devices, and more particularly to gamma ray radioisotope cameras and associated data processing equipment.

2. Description of the Prior Art

A number of radioisotope cameras have been developed for viewing the distribution of radioisotope materials in the bodies of humans and other animals. Such cameras record the entire field of view continuously in contrast to the somewhat older technique of scanning the subject point by point. Radioisotope cameras have become commonplace for diagnositic and research purposes and are extensively used in hospitals and research orginizations. See e.g. Hal O. Anger, *Radioisotope Cameras*, Chapter 19, Instrumentation in Nuclear Medicine, Academic Press, Inc. 1967.

In particular, the gamma ray scintillation camera has become the most commonly utilized radioisotope camera because of its sensitivity and adaptability. The scintillation camera employs a solid sodium iodide scintillation crystal which gives off a point flash of visible light when a gamma ray impinges upon it. An array of photomultipliers tubes are spaced behind the sodium iodide crystal and perform the function of translating the point flashes of light to a pulse of electric current at the outputs of the photomultiplier tubes. The magnitude of the pulse of output current at each tube in the array is proportional to the amount of light which strikes the tube. The position of a single flash of light in the sodium iodide crystal can be determined by comparing the magnitude of the outputs of each photomultiplier tube in the array, since each photomultiplier tube will receive an amount of light from the flash which depends upon the angle and distance of the point flash from the tube. The outputs of the photomultiplier tube can be combined by means of electronic circuitry to yield output signals which are proportional to the position coordinates of the point flash of light, and the intensity of the flash of light. The "picture" seen by the camera may be viewed by utilizing these signals to provide the X and Y inputs to an oscilloscope, with the electrical signal corresponding to intensity being used to control the electron beam intensity of the oscilloscope. The gamma ray image may be focused upon the sodium iodide crystal by means of a pinhole collimator, or more commonly, by means of a multi-channel collimator having numerous channels formed in a gamma ray absorber plate.

The output signals from the gamma ray scintillation camera may also be utilized to provide quantitative information in addition to the pictorial display of the density of gamma ray emissions in a subject. This may be accomplished by feeding the outputs of the gamma ray camera to a digital computer for processing. The signals corresponding to the X and Y location of the flash of light, and the signal corresponding to the magnitude of the flash, are digitized before being supplied to the computer. For purposes of the computing scheme, the recording face of the gamma ray camera is commonly divided up into a rectangular grid containing a large number of small rectangular cells. The computer determines, from the input signal supplied to it from the gamma camera, at which cell on the face of the gamma camera the point flash ocurred. The computer is capable of counting the number of flashes that occur in each cell over a specified period of time, such as one second, and will maintain this number in the memory of the computer. The computer will then begin counting over again for each cell for another predetermined unit of time to determine the number of point flashes occurring at that cell over that unit of time. It is thus possible to have the computer read out the number of gamma point flashes that occurred in any particular cell as a function of time. It is also possible to read out the number of point flashes that occurred in any desired group of cells as a function of time. This procedure is of special value in the examination of dynamically active body organs such as the heart and the kidneys. It is possible, for example, to delineate the area of a gamma ray camera image which corresponds to a ventricle of the heart. The flow of blood containing a radioactive isotope through the ventricle can then be measured by using the computer to determine the change in the number of gamma ray emissions seen by the camera in the area of the ventricle as a function of the time. The internal programming of the computer can be utilized to allow selection of the cells that correspond to the ventricular area of the heart.

It is ofter desirable to correlate the dynamic information obtained from the gamma ray camera pictures of an organ with other physiological data information concerning that organ, or concerning related body function, which are obtained from other physiological sensors. For example, it is desirable to be able to correlate blood pressure and electro-cardiogram (ECG) readings in time synchrony with the gamma ray scintillation camera data concerning the flow through a heart ventricle. It is extremely difficult to acquire the data from the various sensors first, and then attempt to correlate them in time synchrony at a later time. It would be highly desirable to be able to provide the physiological data from the sensors to the computer at the same time that the data is being provided thereto by the gamma ray camera. However, this would require an extensive modification of existing computers, or the use of a larger and more expensive computer with more extensive programming. Such modicications are difficult to implement and have been prohibitively expensive for the common medical applications of the gamma ray camera.

SUMMARY OF THE INVENTION

I have invented a method and a device for the multiplexing of time varying amplitude physiological data signals with the signals that are provided to a data processing computer from the photomultiplier tubes of a gamma ray camera. The physiological data signals are provided for processing by the computer without the necessity for modifications of the gamma ray camera circuitry, or of the hardware or programming of the computer. The processed physiological data signals may be displayed on the readout from the computer in time synchrony with the data obtained from the gamma ray camera pictures.

The signal obtained from a physiological signal source such as a blood pressure sensor, will typically vary in amplitude as a function of time. The voltage or current amplitude may be generally vary between positive and negative values. By the method of my invention, these time varying signals are converted to a series of pulses of uniform shape wherein the pulse frequency varies in direct relation to the amplitude of the physiological signal source. The series of pulses are then each individually shaped to correspond to the width and shape of pulses which are produced by the output circuitry of a photomultiplier tube of the gamma ray camera, such that the physiological signal pulses can be combined with the signal pulses from one of the photomultiplier tubes in the outer ring of tubes. The resulting combined signal is provided to the remaining circuitry of the gamma ray camera and thence to the computer for data processing.

A device for multiplexing physiological signals in accordance with my invention is capable of accepting physiological signals which vary between positive and negative amplitudes. Offset circuitry in my device is utilized where necessary to provide an offset to the physiological signal to ensure that the amplitude of the signal remains uniform in sign, either positive or negative, at all times. The offset signal is then provided to an amplitude to frequency converter which generates uniformly shaped pulses corresponding in frequency to the amplitude of the offset physiological signal. The uniformly shaped pulses of varying frequency are operated upon by a pulse shaping circuit which gives the individual pulses the general shape of pulses emanating from the output circuitry of the photomultiplier tubes. The pulse shaping circuit also is capable of adjusting the amplitude of the pulses to correspond to the pulse amplitude "window" of pulses which are accepted by the gamma ray camera circuitry and data processing circuitry.

The computer interprets the physiological signal information provided through the multiplexing device to an outer photomultiplier tube output as gamma ray scintillations occurring at a single cell along the outer regions of the gamma ray camera image. These outer regions are usually not subjected to gamma ray scintillations since the scintillation crystal is conventionally circular, while the computer is conventionally programmed to store and display the gamma ray scintillation information as a rectangular field. The portion of the display field that is unused for ordinary gamma ray scintillations is thus available for acceptance and storage of the physiological data provided by one or more multiplexing devices. The computer can then be instructed to analyze the physiological signal data contained in the appropriate cell, and display this information as a function of time. The quantitative information obtained from the gamma ray camera pictures may thus be dislayed in time synchrony with the physiological signal source data, and the computer may further be programmed to time correlate the data from the gamma ray camera images with the physiological signal source data. Physiological signal pulses may also be combined with the pulse output from inner photomultiplier tubes where this will not interfere with the gamma camera picture data.

Further objects, features and advantages of my invention will be apparent from the following detailed description taken in conjunction with the accompanying drawings illustrating a preferred embodiment of a method for the multiplexing of physiological signals and a device for the application thereof exemplifying the principles of my invention.

DESCRIPTION OF THE PREFERRED EMBODIMENT

Figure 1:
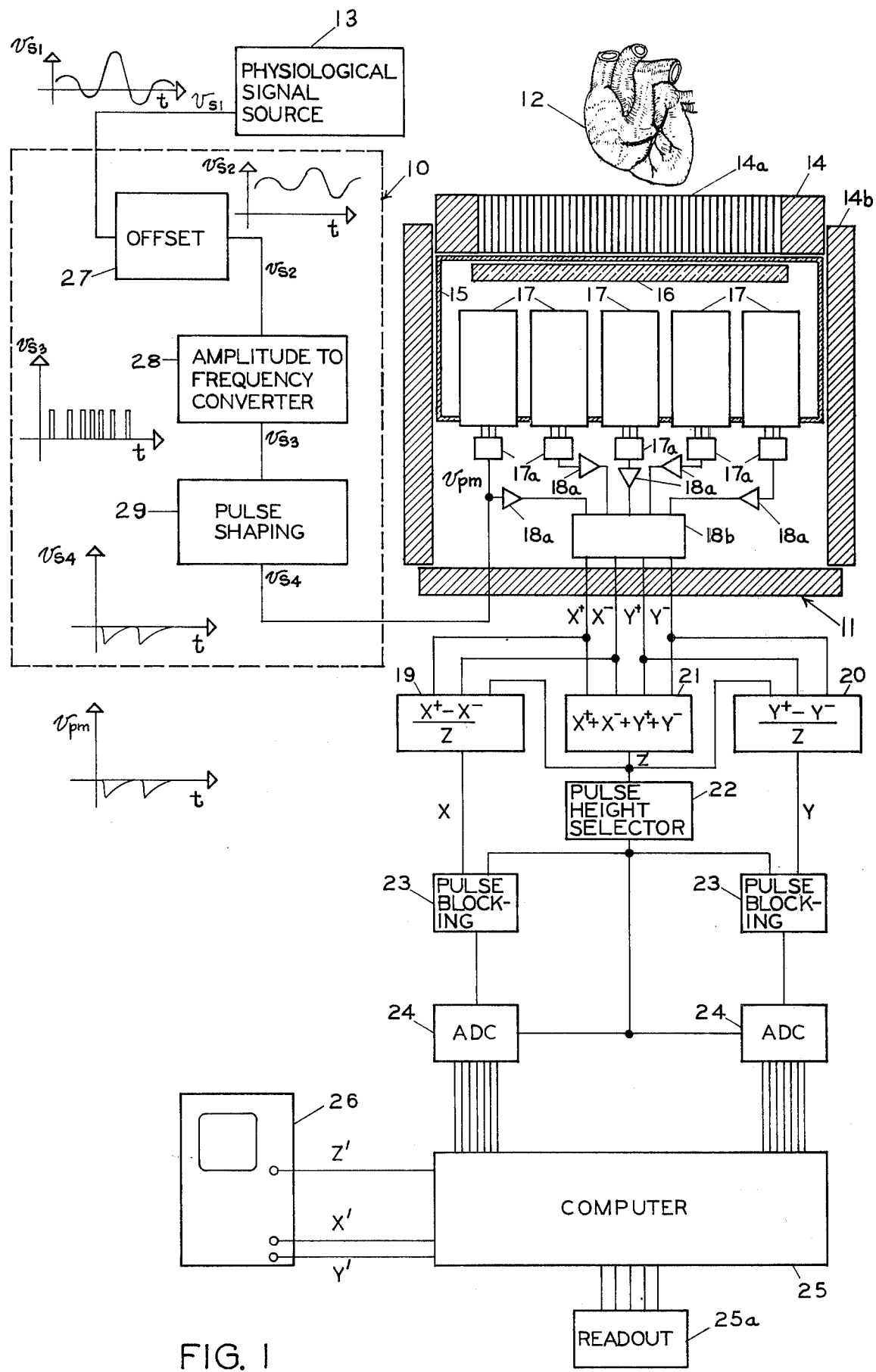
FIG. 1 is a schematic view of my multiplexing device shown in conjunction with a gamma ray scintillation camera as its associated circuitry, and a data processing computer.

Referring now more particularly to the drawings, wherein like numerals refer to like parts throughout the several views, a perferred embodiment of a multiplexing device exemplifying the principles of my invention is shown generally within the dashed lines at 10 in FIG. 1. The multiplexing device 10 is suitable for use with a standard gamma ray scintillation camera shown generally at 11. The gamma camera 11 is utilized to obtained pictures in vivo of the movement of radioisotope materials through the body of a subject. For example, the gamma camera may be directed to observe the passage of an intravenous injection of $^{99m}$TcO-4 through the passageways of the heart, which is represented pictorially at 12 in FIG. 1. Other related body functions may be monitored by means of sensors which provide a continuously time varying electronic signal corresponding to the body function. Such a physiological signal source is shown at 13 in FIG. 1, and may, for example, provide such physiological signals as electracardiogram (ECG) or carotid artery pulse. Other physiological signals are relevent where study of other body organs is involved, such as the tracing of the flow of blood containing a radioisotope through the lungs, which would make time varying pneumotach and blood gas information relevent to the lung study.

The functioning of the gamma ray scintillation camera and the associated data processing epuipment may be illustrated with reference to FIG. 1. The view of the gamma camera shown in FIG. 1 is a somewhat simplified cross sectional view of a typical gamma camera with only the more significant elements of the camera being shown therein. Gamma ray radiation emanating from the area of the heart 12 passes through a collimator 14 which consists of a slab of lead or tungsten having numerous narrow holes or channels 14a formed therein. The channels 14a allow gamma rays that are traveling in alignment with the longitudinal axis of the channels to be passed therethrough, while gamma ray which travel at an angle to be longitudinal axis of the channels will be substantially absorbed by the lead or tungsten walls of the channel. Lead shielding 14b encloses the camera to prevent the entry of stray radiation. Those gamma rays which pass through the collimator will pass through a protective glass envelope 15 and strike a solid sodium iodide (NaI) crystal 16. The gamma rays reaching the sodium iodide crystal are produced as a result of radioactive distintegrations, and consist of descrete photons. The gamma ray produces a point flash of light substantially in the visible range in the sodium iodide crystal at the position where it impinges upon the crystal, with the strength of the light emitted being proportional to the energy of the gamma ray photons striking the crystal. The visible light is emitted isotropically from the point flash, and is transmitted to an array of photomultiplier tubes 17. The photomultiplier tubes 17 are connected to circuitry 17a which provides a high voltage bias to the tubes. When visible light impinges upon the face of the photomultiplier tubes, an output voltage $V_{pm}$ is provided by the circuitry 17a. The output voltage $V_{mp}$ is provided in the form of a pulse of voltage, with the height of the pulse being proportional to the intensity of the light that strikes the photomultiplier tube, and with the width of the pulse being proportional to the length of time that the flash of light persists. In general, the flashes of light resulting from the gamma ray scintillation in the sodium iodide crystal produce short pulses of nearly uniform length. When a single point flash of light occurs in the scintillation crystal, each of the photomultiplier tubes will produce an output pulse, with the height of the output pulse from any given photomultiplier tube being proportional to the intensity of the point flash of light and to be distance of the photomultiplier tube from the point flash. Thus, while all of the photomultiplier tubes will put out a pulse of voltage when a point flash of light occurs in the scintillation crystal, the photomultiplier tube closest to the point flash will put out the largest pulse while the photomultiplier tube farthest away from the point flash will put out a much smaller pulse.

The output signals from the photomultiplier tubes are fed through isolation preamplifiers 18a into a network 18b which forms a portion of the internal circuitry of the gamma ray camera 11. The network 18b operates on the input pulses provided by all of the photomultiplier tubes to yield four outputs signals which are customarily denoted $X^+$, $X^-$, $Y^+$, and $Y^-$ 83, as shown in FIG. 1. These four signals may be utilized to yield the X and Y coordinates of the point flash of light in the crystal and to determine the magnitude of the flash of light. This is done by feeding the $X^+$ and the $X^-$ inputs into a difference circuit 19, by feeding the $Y^+$ inputs and the $Y^-$ inputs into a difference circuit 20, and by feeding all four inputs into an addition circuit 21. The addition circuit 21 adds up all four inputs to provide a voltage signal pulse, labled Z in FIG. 1, with the signal Z being proportional to the magnitude of the point flash of light. The difference circuit 19 subtracts the $X^-$ signal from the $X^+$ signal and divides by the Z signal to yield a pulse output that is proportional in height to the X position of the pulse of light in a rectangular coordinate system. Similarly, the difference circuit 20 subtracts the $Y^-$ signal from the $Y^+$ signal and divides by the Z signal to yield a signal Y which consists of pulses which are proportional in height to the Y coordinates of the point flashes of light. Since a good deal of background radiation and cosmic radiation at low levels finds its way into the gamma camera, it is desirable to be able to filter out these pulses which do not correspond to the gamma rays being emitted from the radioisotopes. It is also desirable to eliminate oversize pulses which may overload the data processing circuitry. This may be accomplished by utilizing a pulse height selector 22 which will transmit a Z pulse only if the pulse is within a pulse "window," with an acceptable pulse exceeding a predetermined threshold magnitude but being less than a predetermined maximum magnitude. The Z signal pulses which are transmitted by the pulse height selector 22 may be used, if desired, to select only those X and Y pulses which correspond to a pulse of significant magnitude by means of pulse blocking circuits 23 which may consist of a modified linear gate controlled by the Z pulse.

Since the X, Y, and Z signals are to be supplied to a digital computer, it is necessary to convert the pulses of varying magnitude to digitally encoded pulse information. This may be accomplished by means of analog-to-digital converters 24 which convert the maximum magnitude of each pulse to a binary coded pulse sequence. These binary signals are then fed into a computer 25. The Z pulse is preferably provided to the analog-to-digital converters 24 to enable the converters only when a Z pulse is present.

The computer 25 is a special purpose digital computer which has the capability of analyzing the binary information concerning each X and Y pulse and assigning each pulse a position corresponding to the cell on the grid of the gamma camera at which the point flash of light occurs. The computer also has the capability of counting the number of pulse that occur within each grid cell on the face of the camera over some given period of time and storing these counts for future reference. The computer may store this information as a "frame," consisting of the number of pulses occurring in each cell of the grid on the face of the gamma camera over the given period of time. This information may be displayed on an oscilloscope as shown in FIG. 1 by providing X' and Y' signals from the computer to the oscilloscope corresponding to the position of a cell, and providing a single Z' which modulates the electron beam intensity of the oscilloscope. The intensity signal Z' is proportional to the number of pulses that were recorded in a given cell over the time period of the frame. A typical picture of a frame as seen on the face of the oscilloscope is shown illustratively in FIG. 3, with the picture representing passage of a radioisotope gamma ray emitting material through the chambers of the heart of a subject. The darker areas shown in FIG. 3 correspond to the heart, with the lightly scattered dots surrounding the heart corresponding to a residual level of background radiation. The encircled area labeled A in FIG. 3 corresponds to the left auricle area of the heart through which the bulk of the intravenous fluid containing the radioisotope is passing at the time that this picture has been taken. The encircled area labeled B corresponds to the left ventricle area of the heart. The computer can be instructed to compute the total pulse count of the areas contained within the encircled regions marked A and B in FIG. 3, and to plot these counts as a function of time. This information can be utilized to determine the flow rate through the auricle and ventricle and to thus display graphically the functioning of the heart muscle and the valves within the heart.

The above described operation of the gamma ray scintillation camera in conjunction with the data processing capabilities of a digital computer are well known techniques, and have been commonly utilized to provide diagnostic information to phyicians in clinical situations. A significant need has been perceived to be able to correlate the information that is obtained from the gamma ray camera and processed by the computer with other time varying physiological signals. For example, it is desirable to time correlate the flow rate through the chambers of the heart with the ECG and carotid artery pulse, to thereby accurately specify the relationship of the opening and closing of the heart valves to the muscular contractions of the heart and the flow of blood out of the heart. If such data are available, the computer itself may be programmed to operate on the various signals to correlate the time varying signals with the data from the gamma camera and to detect abnormalities. One possible method of providing the time varying physiological signals to the computer is by digitizing such signals and introducing the digitized signals into the computer memory in parallel with the signals from the gamma camera. However, to accomplish this result, an extensive modification of the programming of the computer would be required since computers presently used for such applications and their programming are capable of only handling serial input data. Modifications would be required to provide the physiological signal data to the portion of the computer memory assigned to the particular time frame which corresponds to the time at which the physiological signal is sampled. Most of the computers presently being used for gamma ray camera data processing are small, special purpose computers which have limited core memory specifically assigned to storage of sequential frames of data provided from the gamma ray camera.

Figure 3:
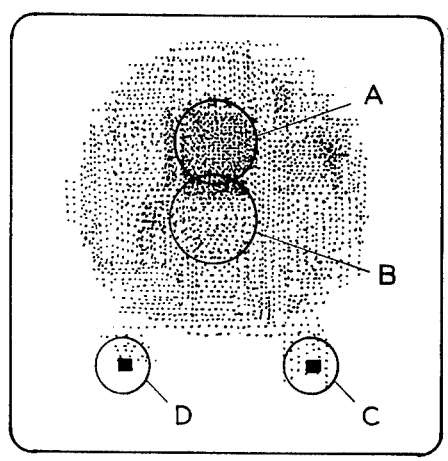
FIG. 3 is an illustrative pictorial representation of a gamma ray scintillation picture as shown on the face of an oscilloscope provided with gamma ray scintillation data from the computer.

My multiplexing device allows the physiological signal source to be multiplexed with the signals provided by the gamma ray camera 11, with the signals being provided in a form which allows their processing by the computer without modification of the hardware or the programming of the computer. My multiplexing device is shown generally in block diagram form within the dashed lines labeled 10 in FIG. 1. A signal is received from the physiological signal source 13 which varies in voltage or current amplitude as a function of time. By the method of my invention, the signal provided by the signal source is converted from a signal that varies in amplitude with time to a pulse frequency modulated signal, with the frequency of the uniformly shaped output pulses varying in direct relation to the amplitude of the physiological source input. It can be seen that if the physiological signal source varies slowly over time compared to the average frequency of the pulses produced, the number of pulses produced over a relatively short segment of time will be approximately proportional to the amplitude of the physiological input signal at that time. These pulses may then be conbined with the outputs pulses from the output circuitry 17a of the photomultiplier tubes 17. If the shape and magnitude of the pulses provided by the multiplexing device 10 are sufficiently similar to the pulses provided by the photomultiplier tubes, the computer will recognize these pulses as being caused by point flashes of light in the scintillation crystal and will assign these pulses to a particular cell and count the number of pulses per a given unit of time. The pulses corresponding to the physiological signal are preferably supplied to the output circuitry of only a single photomultiplier tube, with the computer assigning the physiological signal pulses to a single cell of the camera face grid. If the photomultiplier tubes to which the physiological signal source are applied are among the outer ring of photomultiplier tubes, the cells chosen will be outside of the gamma camera field of view. As shown in FIG. 3, the outer portions of the grid rarely or never are found to have gamma ray induced flashes occurring to those points. This ordinarily unused space exists because the grid on the face of the camera is divided into a rectangular coordinate system whereas the scintillation crystal is circular, leaving a dead space between the crystal and the boundaries of the rectangular coordinate system. Thus, supplying the physiological data signals to the output circuitry of a single outer photomultiplier tube will not substantially interfere with the recording of the gamma ray scintillation data.

In general, the output signal $V_{s1}$ from the physiological signal source 13 may vary in signal between positive and negative values. In order to ensure that the signal does not change in sign before it is converted to a frequency modulated series of pulse, the signal $V_{s1}$ is provided with an amplitude offset by an offset circuit 27. The offset circuit 27 puts out a signal $V_{s2}$ which is always of one sign, preferably positive, and which consists of a signal $V_{s1}$ plus a DC bias at least as great as the maximum of the signal $V_{s1}$. The offset circuit is preferably capable of being adjusted to adapt to signal source having positive and negative signal ranges of varying maximum amplitudes. Of course, if the physiological signal source 13 produces a signal which is always positive or negative, the offset circuit is unnecessary and may be bypassed.

The output of the offset circuit is then fed into the amplitude-to-frequency converter 28 which converts the time varying magnitude signal $v_{s2}$ to a series of uniformly shaped pulses. The spacing between the uniform pulses in the output signal $V_{s3}$ of the amplitude-to-frequency converter 28 is inversely proportional to the magnitude of the time varying signal $V_{s2}$. The amplitude-to-frequency converter 28 is preferably set such that the average frequency of the pulses in the output signal $V_{s3}$, corresponding to the average amplitude of the input signal $V_{s2}$, is substantially greater than the highest significant frequency contained in the physiological input signal $V_{s1}$. This condition is not difficult to meet since most physiological signals such as ECG and blood pressure will have a period of a quarter second or more. The amplitude-to-frequency converter 28 may easily be set to provide pulse frequencies in the range of 100 pulses per second to 1,000 pulses per second or more. The number of frames per second analyzed by the computer should also be substantially greater than the highest significant frequency, preferably being at least twice as great. The number of physiological signal pulses should be kept substantially lower than the approximately 20,000 pulses per second of gamma ray scintillation data to avoid overloading the gamma camera and data processing circuitry and thereby degrading the gamma camera picture.

As indicated above, the output pulse from the photomultiplier tube 17, as provided by the output circuitry 17a, will have a substantially uniform pulse rise time and fall time and a varying pulse height. The network 18b and the subsequent difference and addition circuitry are adapted to operate on pulses of such shapes. Thus, it is desirable that the pulses from the multiplexing device 10 have about the same shape, i.e. rise and fall time, as the pulses that are provided by the out put circuitry 17a of the photomutiplier tubes. The height of the pulses supplied by the multiplexing device must also be of an amplitude which falls within the band of amplitudes accepted by the pulse height selector 22 so that all of these pulses are received by the computer for processing. This adjustment of the pulses provided by the amplitude to frequency converter is obtained in a pulse shaping circuit 29 which provides a shaped pulse output $V_{s4}$. The output signal $V_{s4}$ is then transmitted to the output circuitry 17a of an outer photomultipier tube and is combined with the photomultiplier tube output signal $V_{pm}$. The output signal $V_{s4}$ may be combined with the signal $V_{pm}$ by simply connecting together the output leads carrying these signals before the signals are fed to the isolation preamplifier 18a. Where such an isolation amplifier is not provided as part of the internal circuitry of the gamma camera, it is desirable to provide such isolation amplfier or, alternatively, to combine the two signals with an adder. The physiological data signal pulses are then fed into the computer along with the gamma ray signals, and are processed in the manner described above and assigned to specific cells in the grid.

Figure 4:
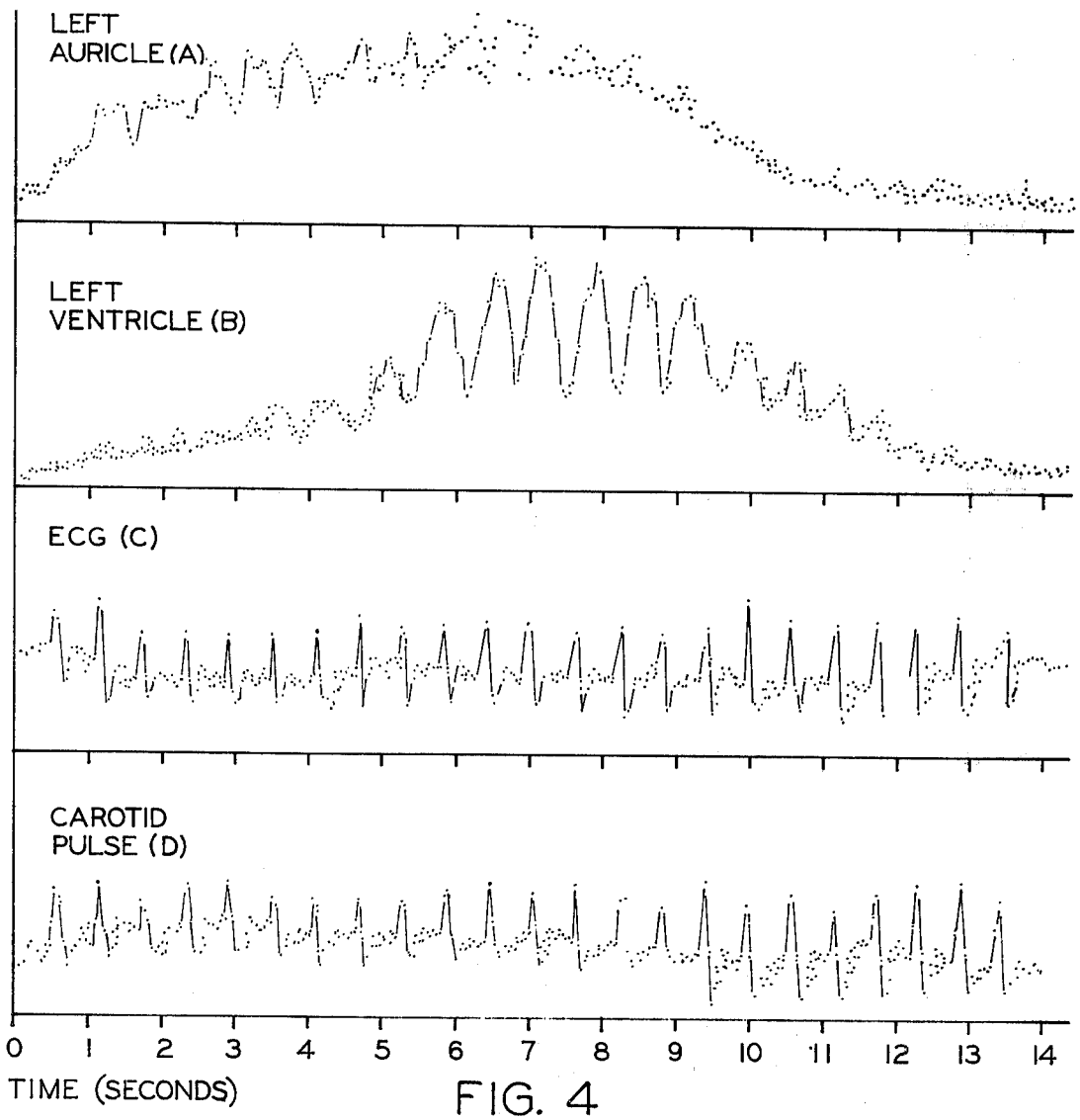
FIG. 4 is an illustrative representation of the data obtained from gamma ray scintillation camera pictures shown in time synchrony with physiological data signals which have been multiplexed with the gamma ray scintillation signals.

Referring to FIG. 3, the introduction of two physiological data signals to two chosen outer photomultiplier tube outputs results in the placement of a physiological data information in the encircled areas labeled C and D on the face of the oscilloscope 26. For example, the information contained in the encircled area marked c may correspond to ECG data and the area marked D may correspond to carotid artery pulse. The computer may be commanded to analyze the encircled areas marked A, B, c, and D and to plot this data as a function of time on a read-out device 25a, which may be a line printer or strip chart recorder. The data may also be plotted on the face of the oscilloscope, with a photograph being taken of the oscilliscope plot. An example of such an output plot is given in FIG. 4, in which a frame of data is taken every 50 msec. (1/20 of a second) on the gamma ray camera, and with the ECG signal and the carotid pulse signal being sampled every 50 msec. in time synchrony with the frames taken on the gamma camera. the relationship as a function of time between the ECG data, the carotid pulse data, the flow through the left auricle, and the flow through the left ventricle are clearly shown in the plot given in FIG. 4. Such a plot allows a physician or diagnostician to easily compare the various physiological signals and detect the presence of abnormalities. Such data may also be further processed by the computer to correlate the various data signals as a function of time and thus provide for a computer diagnosis of abnormalities or dysfunctions.

Figure 2:
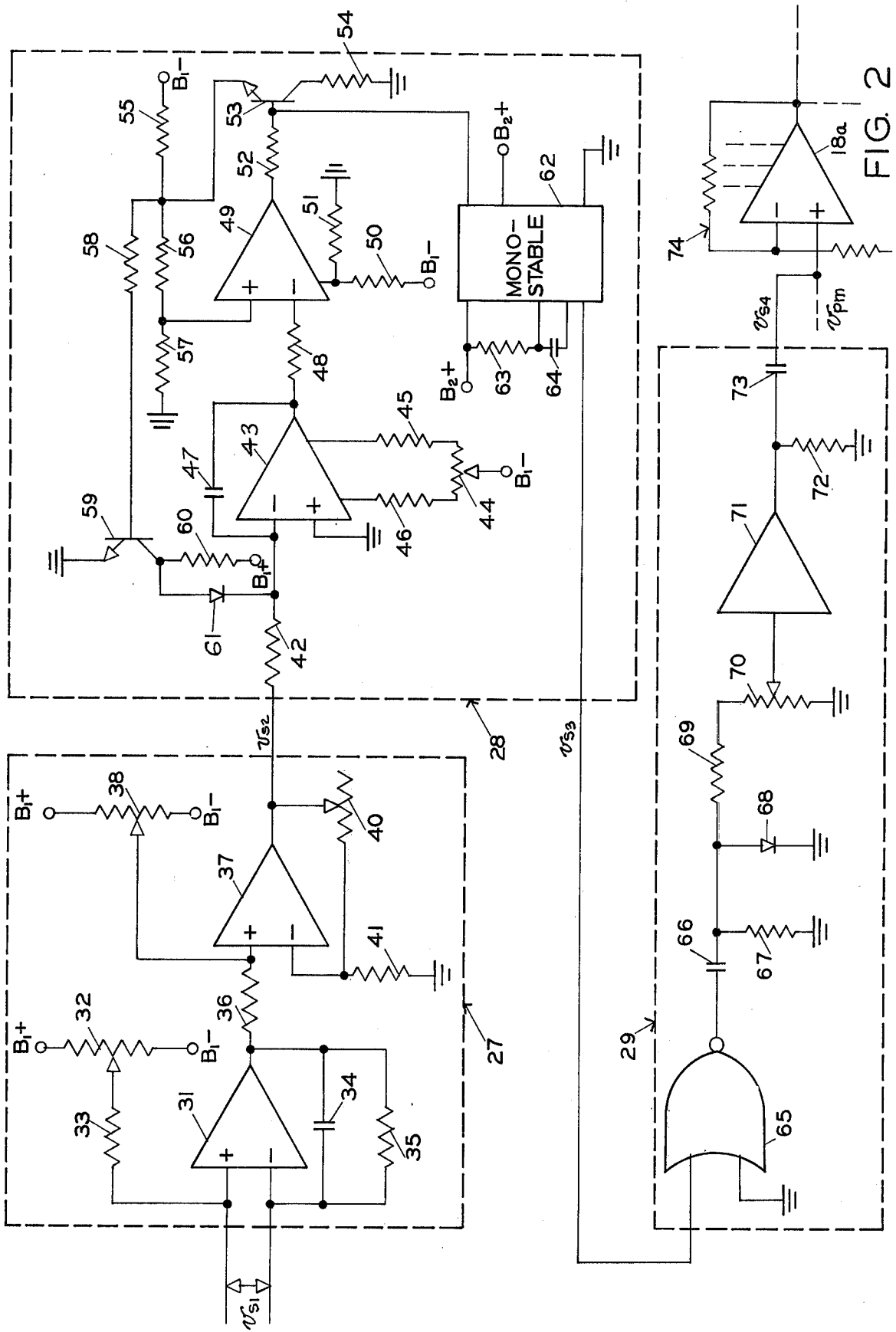
FIG. 2 is a schematic circuit diagram of an illustrative embodiment of the circuitry for my multiplexing device.

By way of specific illustration, an example of a multiplexing device capable of providing satisfactory pulse input signals to a commercially available gamma ray camera (Radiacamera II) is shown schematically in FIG. 2 The device shown in Fig. 2 can also be used with other commercially available cameras by adjusting the width and magnitude of the output pulses provided by the device. As shown in FIG. 2, the physiological data signal $V_{s1}$ consisting of a time varying voltage amplitude is provided to the offset circuit shown within the dashed lines labeled 27. The offset circuit 27 consists of a first differential operational amplifier 31, with two input lines carrying the data signal $V_{s1}$ being provided to the + and − inputs of the amplifier 31. An adjustable voltage bias is provided to the + input of the amplifier 31 by a potentiometer 32 provided with bias voltage $B_{1+}$ and $B_{1-}$, through a resistor 33. Feedback to the − input is provided from the output of the amplifier 31 by a capacitor 34 and a feedback resistor 35 in parallel therewith. The output of the amplifier 31 is fed through a resistor 36 to the + input of a second differential operational amplifier 37. The positive input of the amplifier 37 is also biased with voltage provided through a potentiometer 38 provided with sources of bias voltage $B_{1+}$ and $B_{1-}$. The output of the amplifier 37 is fed back through a potentiometer 40 forming a voltage divider with a resistor 41 to ground. The output of the biasing amplifier 27, $V_{s2}$, is adjusted to always remain positive, for the range of voltages $V_{s1}$ expected, by means of the potentiometers 32, 38, and 40.

The output signal $V_{s2}$ of the offset circuit is fed to the input of the amplitude to frequency converter shown within the dashed lines labeled 28 in FIG. 2. The signal $V_{s2}$ is fed through a resistor 42 to the − input of a differential operational amplifier 43. The + input of the amplifier 43 is connected to ground as shown. The bias voltage of the operational amplifier 43 is adjustable by means of a potentiometer 44 connected to the source of voltage $B_{1-}$, with the bias voltage being provided to the operational amplifier through resistors 45 and 46. The output of the amplifier 43 is fed back to the negative input thereof by means of a capacitor 47, which provides, in the absence of other inputs, an integration at the output of the amplifier 43 of the signal $V_{s2}$. The output of the amplifier 43 is provided through a resistor 48 to the − input of a voltage comparator 49. The comparator 49 is provided with bias voltage from a source of negative voltage $B_{1-}$ through a voltage divider consisting of resistors 50 and 51. The output of the comparator 49 is fed through a resistor 52 to the base of a transistor 53. The collector of the transistor 53 is connected to ground through a resistor 54, while the emitter is connected through a resistor 55 to a source of negative voltage $B_{1-}$. The output of the emitter is also fed back through a voltage divider consisting of resistors 56 and 57 to the + input of the comparator 49. The output of the comparator 49 is either "high" or "low" depending on the relative magnitudes of the signals at the + and − inputs to the comparator. The output of the emitter of the transistor 53 is fed through a resistor 48 to the base of a transistor 59. The emitter of the transistor 59 is connected directly to ground, while the collector is provided with a source of positive voltage $B_{1+}$ through a resistor 60. The collector voltage of the transistor 59 is fed through a diode 61 back to the − input of the amplifier 43.

The output of the comparator 49 consists of a series of pulses of substantially uniform height and of somewhat varying pulse widths, with the frequency of the pulses being proportional to the amplitude of the signal $V_{s2}$.

The output signal from the comparator 49, after passing through the resistor 52, is provided to the input of a monostable multivibrator 62. The monostable 62 is provided with a bias voltage $B2_+$ and triggers at a low input voltage and generates a pulse having a relatively narrow pulse width determined by the value of a resistor 63 and a capacitor 64. The input provided to the monostable may vary somewhat in pulse height and width. However, the monostable triggers on the leading edge of the input pulses and puts out a series of uniformly shaped rectangular pulses with the frequency of the output pulses corresponding to the frequency of the input pulses.

The output signal $V_{s3}$ of the monostable, which consists of a series of pulses varying in frequency over time, is provided to the input of the pulse shaping circuit 29. As indicated above, the purpose of the pulse shaping circuit is to modify the shape of the pulses provided by the amplitude-to-frequency converter 28 such that the output pulses will correspond generally in height and rise and fall time to the pulses generated by the photomultiplier tubes at the particular point in the gamma camera circuitry at which the physiological signal pulses are to be combined therewith. It has been generally observed that, although the output pulses from the photomultiplier tubes vary in maximum amplitude, the pulses have substantially the same shape of an exponential rise toward a constant value and an exponential fall with substantially the same rise and fall time constants. The physiological signal pulses should tend to match this shape. The pulse shaping circuit 29 has a NOR gate 65 which receives the voltage pulse signal $V_{s3}$ at one high impedance input, with the other input of the NOR gate 65 being connected to ground. For convenience, the inverting output of the monostable 62 is connected to the NOR gate, with this output providing a normally high signal with uniformly shaped "low" pulses. The NOR gate provides a low impedance output signal which is normally low, with the output going "high" when a pulse from the monostable is received at the input to the NOR gate. The output of the NOR gate is fed through a differentiating circuit which consists of a series capacitor 66 and a resistor 67 running to ground. A diode 68 is connected in parallel with the resistor 67 to ground to eliminate any positive voltage pulses at that point in the circuit. The negative voltage output pulses are then passed through a voltage divider consisting of a fixed resistor 69 and a potentiometer 70, with the wiper of the potentiometer being connected to the input of a noninverting driver amplifier 71. The output of the amplifier 71 is fed through a load resistor 72 to ground, with the time varying portion of the output of the amplifier being passed through a coupling capacitor 73 to the input of an isolation preamplifier 18a which forms a portion of the gamma camera circuitry partially shown at 74 in FIG. 2. The signal $V_{s4}$ consists of a series of uniformly shaped smooth pulses which vary in frequency over time, in accordance with the magnitude of the voltage input $V_{s1}$. As shown in FIG. 2, the signal $V_{s4}$ may be combined with the photomultiplier output signal $V_{pm}$ at that point in the gamma camera circuitry by connecting the output lead from the pulse shaping circuit to the lead carrying the signal $V_{pm}$ into an input of a preamplifier. The combined output signal from the gamma camera preamplifier will consist of the $V_{pm}$ signal pulses from the photomultiplier tube interspersed with the $V_{s4}$ signal pulses from the physiological signal source. There will be only a small liklihood of interference between the pulses provided by the photomultiplier tubes and the pulses originating from the physiological signal source. The pulse width of all pulses will be a few microseconds at most with the spacing between pulses averaging several hundred microseconds.

For purposes of illustration, component values for an example of an operable embodiment of the circuit shown in FIG. 2 are given in Table I below.

Table I

| | |
|---|---|
| Operational amplifier 31 | Type 747 |
| Potentiometer 32 | 10,000 ohms |
| Resistor 33 | 47,000 ohms |
| Capacitor 34 | 680 picofarads |
| Resistor 35 | 47,000 ohms |
| Resistor 36 | 47,000 ohms |
| Operational amplifier 37 | Type 747 |
| Potentiometer 38 | 5,000 ohms |
| Potentiometer 40 | 50,000 ohms |

Table I-continued

| | |
|---|---|
| Resistor 41 | 4,700 ohms |
| Resistor 42 | 33,000 ohms |
| Operational amplifier 43 | Type 741 |
| Potentiometer 44 | 2,500 ohms |
| Resistor 45 | 47,000 ohms |
| Resistor 46 | 47,000 ohms |
| Capacitor 47 | 0.001 microfarads |
| Resistor 48 | 1,000 ohms |
| Comparator 49 | Type 710 |
| Resistor 50 | 680 ohms |
| Resistor 51 | 620 ohms |
| Resistor 52 | 1,000 ohms |
| Transistor 53 | Type 2N5134 |
| Resistor 54 | 5,100 ohms |
| Resistor 55 | 9,100 ohms |
| Resistor 56 | 470 ohms |
| Resistor 57 | 4,900 ohms |
| Resistor 58 | 4,700 ohms |
| Transistor 59 | Type 2N5134 |
| Resistor 60 | 5,100 ohms |
| Diode 61 | Type 1N914 |
| Monostable 62 | Type 74123 |
| Resistor 63 | 22,000 ohms |
| Capacitor 64 | 330 picofarads |
| NOR gate 65 | Type 74128 |
| Capacitor 66 | 0.005 microfarads |
| Resistor 67 | 220 ohms |
| Diode 68 | Type 1N914 |
| Resistor 69 | 22,000 ohms |
| Potentiometer 70 | 10,000 ohms |
| Amplifier 71 | Type LH002 |
| Resistor 72 | 50 ohms |
| Capacitor 73 | 60 picofarads |
| Supply voltage $B_1+$ | +15 volts |
| Supply voltage $B_1-$ | −15 volts |
| Supply voltage $B_2+$ | +5 volts |

Negative pulses are provided by the pulse shaping circuit 29 to correspond to the negative pulses $V_{pm}$ provided to the preamplifier 18a by the output circuit of the photomultiplier tubes of the particular gamma ray camera considered here for exemplification (General Electric Radicamera II). It is apparent that positive pulses could be provided if a gamma ray camera was utilized which provided positive pulses at the photomultiplier tube output circuitry. The values given for the capacitors 66 and resistor 67 yield output pulses with a pulse width of 2 to 3 microseconds, which corresponds approximately to an average gamme ray scintillation pulse from the photomultiplier tubes. The value of the coupling capacitor 73 is preferably kept very small to minimize any loading effect that connection of the pulse shaper output to the preamplifier input may have on the photomultiplier tube signal. The height of the pulses passed by the capacitor 73 may be adjusted by means of the potentiometer 70 at the input to the amplifier 71 to ensure that the pulses are accepted by the gamma camera and data processing circuitry.

Ordinarily it is preferable to supply the physiological data signal pulses only to the outer photomultiplier tubes so that the gamma ray camera picture is not interfered with. However, there may be portions of the gamma camera picture which are not of interest and physiological data could be placed at these locations by supplying the data signals to an inner photomultiplier tube. It is also possible to supply data signals to all of the photomultiplier tube outputs for time correllation by the computer if gamma camera pictures are not being taken.

It is understood that my invention is not confined to the particular construction and arrangement of parts herein illustrated and described, but embraces all such modified forms thereof as come within the scope of the following claims.

I claim:

1. A method for multiplexing time varying amplitude physiological data signals with the output signals provided by the output circuitry of the photomultiplier tubes of a gamma ray scintillation camera, comprising the steps of:
   a. providing a physiological data signal having a time varying amplitude which does not change in sign;
   b. generating a series of pulses of uniform shape having a pulse frequency which is directly proportional to the amplitude of said physiological data signal;
   c. shaping said pulses such that each shaped pulse has approximately the same shape as an output pulse provided by the output circuitry of a photomultiplier tube when the photomultiplier tube is struck by light emanating from a gamma ray scintillation; and
   d. combining said physiological data signal pulses with the output pulses from the output circuitry of a photomultiplier tube of said gamma ray camera.

2. A device for multiplexing time varying amplitude physiological data signals with the output signals provided by the output circuitry of the photomultiplier tubes of a gamma ray scintillation camera, comprising:
   a. amplitude to frequency converter means for receiving a time varying amplitude physiological data signal which does not change in sign and for providing a series of uniformly shaped output pulses, the frequency of said series of output pulses being directly proportional to the amplitude of the physiological data signal;
   b. pulse shaping means for receiving said series of output pulses from said amplitude to frequency converter means and for shaping each pulse of said series of pulses to have approximately the same shape as an output pulse provided by the output circuitry of a photomultiplier tube when the photomultiplier tube is struck by light emanating from a gamma ray scintillation; and
   c. circuit means for transmitting said shaped pulses from said pulse shaping means to the output circuitry of a photomultiplier tube such that said shaped pulses are combined with the output pulses provided by the output circuitry of the photomultiplier tube.

3. The multiplexing device specified in claim 2 including offset means for receiving a physiological data signal which varies in sign, for providing the time varying physiological data signal with an amplitude offset such that the offset data signal does not change in sign, and for providing said offset physiological data signal to said amplitude to frequency converter means.

4. An improved radioisotope gamma ray camera data processing apparatus, of the type having a gamma ray scintillation camera including an array of photomultiplier tubes for receiving light emitted from gamma ray scintillations in a crystal and providing electrical pulses at the output circuitry of the photomultiplier tubes when a gamma ray scintillation occurs in the crystal, circuitry for operating on the signals provided by the photomultiplier tubes in the array to produce electrical signals corresponding to the position in the crystal of the gamma ray scintillation, converters to convert the electrical signals corresponding to the position of the gamma ray scintillation to binary encoded data, a computer which receives the binary coded data and assigns the data to a position on the face of the gamma ray camera corresponding to the point of the gamma ray scintillation, and an output device controlled by the computer which provides a display of the number of gamma ray scintillations occurring at selected positions on the face of the gamma ray camera as a function of time, wherein the improvement comprises:
   a. amplitude to frequency converter means for receiving a time varying amplitude physiological data signal which does not change in sign and for providing a series of uniformly shaped output pulses, the frequency of said series of output pulses being directly proportional to the amplitude of the physiological data signal;
   b. pulse shaping means for receiving said series of output pulses from said amplitude to frequency converter means and for shaping each pulse of said series of pulses to have approximately the same shape as an output pulse provided by the output circuitry of a photomultiplier tube when the photomultiplier tube is struck by light emanating from a gamma ray scintillation; and
   c. circuit means for transmitting said shaped pulses from said pulse shaping means to the output circuitry of a photomultiplier tube such that said shaped pulses are combined with the output pulses provided by the output circuitry of the photomultiplier tube.

5. The improved gamma ray camera data processing apparatus specified in claim 4 including offset means for receiving a physiological data signal which varies in sign, for providing the time varying physiological data signal with an amplitude offset such that the offset data signal does not change in sign, and for providing said offset physiological data signal to said amplitude to frequency converter means.

* * * * *

UNITED STATES PATENT AND TRADEMARK OFFICE
CERTIFICATE OF CORRECTION

PATENT NO. : 4,033,335
DATED : July 5, 1977
INVENTOR(S) : Robert J. Nickles

It is certified that error appears in the above-identified patent and that said Letters Patent are hereby corrected as shown below:

Column 1, before "BACKGROUND OF THE INVENTION" insert as the first paragraph:

-- The invention described herein was made in the course of work under a grant or award from the Department of Health, Education, and Welfare.--

Column 2, Line 28 "It is ofter" should be --It is often--;

Column 2, Line 32 "function," should be --functions,--;

Column 2, Line 46 "modicications" should be --modifications--;

Column 2, Line 67 "may be generally vary" should be --may more generally vary--;

Column 4, Line 6 "camera as its associated" should be --camera and its associated--;

Column 4, Lines 41-42 "electracardiogram" should be --electrocardiogram--;

Column 4, Line 49 "epuipment" should be --equipment--;

Column 5, Line 27 "and to be distance" should be --and to the distance--;

Column 5, Line 40 "outputs" should be --output--;

Column 5, Line 41 ", and $Y^-$ 83," should be --, and $Y^-$,--;

UNITED STATES PATENT AND TRADEMARK OFFICE
CERTIFICATE OF CORRECTION

PATENT NO. : 4,033,335
DATED : July 5, 1977
INVENTOR(S) : Robert J. Nickles

It is certified that error appears in the above-identified patent and that said Letters Patent are hereby corrected as shown below:

Column 5, Line 50 "labled" should be --labeled--;

Column 6, Line 26 "pulse" should be --pulses--;

Column 7, Line 52 "the outputs pulses" should be --the output pulses--;

Column 8, Line 13 "may vary in signal" should be --may vary in sign--;

Column 8, Line 16 "pulse" should be --pulses--;

Column 8, Line 22 "source" should be --sources--;

Column 9, Line 1 "adjustment of the pulses" should be --adjustment of the size and shape of the pulses--;

Column 9, Line 21 "placement of a" should be --placement of the--;

Column 9, Line 24 "marked c" should be --marked C--;

Column 9, Line 28 "A,B,c, and D" should be --A,B,C, and D--;

Column 9, Line 38 "the relationship" should be --The relationship--;

UNITED STATES PATENT AND TRADEMARK OFFICE
CERTIFICATE OF CORRECTION

PATENT NO. : 4,033,335
DATED : July 5, 1977
INVENTOR(S) : Robert J. Nickles

It is certified that error appears in the above–identified patent and that said Letters Patent are hereby corrected as shown below:

Column 10, Line 41 "a resistor 48" should be --a resistor 58--;

Column 12, Line 33 "output circuit" should be --output circuitry--;

Column 12, Line 42 "gamme ray" should be --gamma ray--

*Signed and Sealed this*

*Eighth* Day of *November 1977*

[SEAL]

Attest:

RUTH C. MASON
*Attesting Officer*

LUTRELLE F. PARKER
*Acting Commissioner of Patents and Trademarks*